United States Patent [19]

Frontczak

[11] 4,380,551

[45] * Apr. 19, 1983

[54] METHODS OF PRODUCING FOODSTUFF BY MALTING SEEDS

[75] Inventor: Stanisław Frontczak, Lodz, Poland

[73] Assignee: Jacek Długołęcki, Poland; a part interest

[ * ] Notice: The portion of the term of this patent subsequent to Mar. 30, 1999, has been disclaimed.

[21] Appl. No.: 181,816

[22] Filed: Aug. 27, 1980

[30] Foreign Application Priority Data

Jul. 31, 1980 [GB] United Kingdom ................. 8025083

[51] Int. Cl.³ ........................... A23K 1/00; A23K 1/14
[52] U.S. Cl. ......................................... 426/28; 426/44; 426/46; 426/623; 426/630; 426/54; 426/56; 426/555; 426/635; 47/59; 47/14; 47/62; 47/54; 47/16; 47/60; 111/DIG. 1
[58] Field of Search ................. 426/289, 615, 618, 28, 426/54, 46, 44, 635, 59, 61; 47/62, 64, 65, 16, 14, 60; 111/DIG. 1

[56] References Cited

U.S. PATENT DOCUMENTS

| | | |
|---|---|---|
| 1,554,913 | 9/1925 | Grelck ................................... 426/54 |
| 1,848,219 | 3/1932 | Kerr ....................................... 47/14 |
| 2,175,113 | 10/1939 | Fischer ................................... 47/14 |
| 2,178,051 | 7/1940 | Sams .................................... 426/635 |
| 2,810,988 | 10/1957 | Chin ....................................... 47/16 |
| 3,131,064 | 4/1964 | Malchair ................................ 47/59 |
| 4,075,785 | 2/1978 | Jones ..................................... 47/62 |
| 4,322,443 | 3/1982 | Frontczak ....................... 426/623 X |

FOREIGN PATENT DOCUMENTS

| | | | |
|---|---|---|---|
| 1271294 | 4/1970 | France .................................... 47/60 |
| 122947 | 2/1919 | United Kingdom ................... 47/62 |

OTHER PUBLICATIONS

Daniel, Bakery Materials & Methods, Maclaren & Sons Ltd., London, p. 89, 1963.

*Primary Examiner*—Jeanette M. Hunter
*Attorney, Agent, or Firm*—Roylance, Abrams, Berdo & Farley

[57] ABSTRACT

Preparing a foodstuff for human or animal consumption by sowing seeds of at least one quick-germinating plant of a type such as to produce strong root systems in peat which is allowed to lie in a layer having a thickness in the range of from 40 to 200 mm for a vegetation period of from 10 to 21 days, there being at least 900 Kg of seeds per hectare of the layer and recovering the germinated seeds and the peat as the foodstuff.

18 Claims, No Drawings

METHODS OF PRODUCING FOODSTUFF BY MALTING SEEDS

This invention relates to methods of producing foodstuff.

According to the invention there is provided a method of producing foodstuff in which seeds of at least one quick-germinating plant of a type such as to produce strong root systems are sown in peat which is allowed to lie in a layer having a thickness in the range of from 40 to 200 mm for a vegetation period of from 10 to 21 days, there being at least 900 Kg of seeds per hectare of the layer.

The seeds may be sown in a dry condition, or may be sown at the stage of initial germination.

For a better understanding of the invention, and to show how the same may be carried into effect, reference will now be made to a number of examples of methods of producing foodstuff.

Such methods have already been described in United Kingdom patent specification No. 80.02710, publication No. 2,067,883 and the present specification relates to developments of such methods.

Fundamentally, the methods consist in allowing quick-germinating plants to develop in a layer of peat. The resulting mixture of peat and seedlings may be usable as foodstuff.

In a first example, a quantity of disaggregated peat is applied on a surface which is impermeable to plant roots in a layer having a thickness of about 50 mm (2 inches). In the peat layer are sowed seeds in a quantity of about 1000 Kg per hectare. If the ensuing vegetation process is assisted by good irrigation and sufficient sunshine, a vegetation period of 21 days is sufficient to produce about 140 metric tons per hectare of dried fodder.

In a second example, the method is similar to that described in the first example, but seeds are sown in a quantity of about 1500 Kg per hectare and the vegetation period is shortened to 14 days. About 135 metric tons per hectare of fodder in dried form may be obtained.

In a third example, the past will be disposed on an impermeable surface in a layer of about 40 mm thickness. About 1800 Kg per hectare of seeds are sown in the layer. With adequate sunshine and good irrigation, the vegetation period may be completed in 12 days. About 115 metric tons per hectare of fodder (dry weight) may be obtained. This fodder may be used for feeding broilers.

In a fourth example, a layer of peat having a thickness of about 150 mm is disposed on an impermeable surface and plant seeds as sown in as in the third example. The vegetation process is allowed to continue for 14 days. Thereafter, any plant growth protruding above the peat surface is removed. These collected plant portions are cut and dried, the remaining peat layer including the plant root systems subjected to a mixing process. Further seeds are then sown into the remaining layer. A further vegetation process is then allowed to take place for a period of 14 days. The resulting peat plant mass is mixed with the plant material obtained after the first vegetation period. The resulting fodder contains a large percentage of plant material.

In a fifth example, a layer of peat having a thickness of 200 mm is disposed on an impermeable surface and plant seed sown in the layer and allowed to develop undisturbed for 21 days. After this period, any plant matter protruding above the peat surface is collected, disaggregated and dried. The remaining peat layer including the plant root systems is then subjected to a mixing process by means of a harrow or by means of cultivators and thereafter the layer surface is hardened by means of rolling. Further plant seeds are then sown and a further vegetation period of 12 days is allowed. After this period, the resulting peat plant mixture is enriched by the addition of the plant material collected after the first vegetation period.

In a sixth example, a peat layer of 50 mm thickness is disclosed on an impermeable surface. The peat is then initially sterilised by means of ultra-violet radiation applied for a period of 2 minutes. Seeds of plants such as salad plants, sorrel, cabbage and wheat are sown in the peat layer in an amount of about 1 Kg for every ten square meters. Vegetation is allowed to take place for fourteen days at a temperature of from 17° C. to 23° C. Thereafter, the resulting peat-plant mixture is collected and dried, e.g. in a horizontal continuous drying stove. The resulting mixture may be utilised in baking. It may be mixed, in a proportion of 15% by weight, with baking flour.

In a seventh example, the procedure is similar to that explained in example 6. Thereafter, the resulting material is disaggregated and placed in a container to which water containing 3% lime is introduced. After 24 hours, the liquid is drained through a net-like filter. Additives for improving the flavour, such as molasses for example, are then added and the mixture may be used for baking wholemeal bread, or for baking cake, the mixture representing 15% by weight of the total ingredients.

In an eighth example, the procedure is similar to the seventh example but the initial sterilisation is achieved by means of pulses of ultra-violet radiation. Preferably 30 second periods of irradiation are utilised with 30 second intervals. A 60 mm thick layer of peat is disposed on foil and seeds of peas, field peas, and rye are sown in. The vegetation process is allowed to take place for 18 days at room temperature (about 20° C.). The final operations are carried out as in the preceding example. Resulting product may be mixed with barley groats in an amount of 17% by weight.

The ninth example uses a peat layer of 70 mm thickness in which seeds of Hypericum perforatum, maculatum, acutum and hypericum humifusum are sown. The seeds are allowed to germinate for 21 days, and the peat layer including the seedlings is then collected and the mixture crushed. The resulting pulp is again disposed on a foil and further seeds sown. The second vegetation period takes place and the resulting mixture is collected and disaggregated. The resulting mixture is again laid on an impermeable surface and a further sowing is carrier out. A third vegetation process then takes place followed by collection of the layer and disaggregation. The resulting peat-plant mixture is dried and packed.

In a tenth example, the peat-plant producing process is effected as in one of the examples 1 to 5. The resulting mixture is then placed in water containers to allow biological processes to take place for the production of chlorella algae for use as food for higher order living organisms.

In an eleventh example, the peat-plant producing process is carried out as in one of the examples 1 to 5 and the resulting mixture is utilised in a sugar producing process and fermented. The resulting mixture may be distilled to produce a liquid suitable for consumption and/or industrial purposes.

Of course, many variations and combinations of the above described examples are possible in dependence upon particular circumstances.

It will be appreciated that in the case of a relatively thin layer of peat and the short vegetation period the germinating seeds are able to transform practically the whole of the peat layer into an acceptable fodder. This fodder is highly nutritious in that it contains plants in the early stages of their development when they contain enzymes which are an important component of fodder for living organisms. Young plant tissues are not only an easily digestable food, but they are also very beneficial to health. It is thought that they may result in improved appetite, and may stimulate vital processes such as fertility and sexual activity, may improve the effectiveness of fertilisation, as well as generally contributing to improved growth and development. The presence of particularly suitable dietry components in the peat including its micro-organisms results in further beneficial properties of the fodder. Some properties of the peat derive from the way in which it is formed from swamp plants as a result of biochemical processes in anaerobic conditions. The plant material of the peat becomes enriched with carbon, nitrogen and other chemical components. As a result, the organic peat substance is composed of bitumens, humic acids and their salts, hemicellulose, lignin and protein compounds. These substances are the components of the peat having food value. As well as the presence of these substances, as a result of the initial stages of plant growth in the peat, considerable quantities of enzymes and other biological substances are produced. The combination of these two groups of components: peat and young plants, results in a mixture of considerable alimentary value.

As will be recalled from the examples described above, in some methods the peat layer may be utilised twice. After disposing the peat layer in a thickness of from 40 to 200 mm on an impermeable surface and sowing plant seeds therein, a vegetation period of below 22 days is permitted and thereafter plant matter is collected from the peat surface. This collected green fodder is dried and the remaining peat layer mixed and hardened. Then further plant seeds are sown in this layer. The second vegetation period then occurs, which also is completed in a time less than 22 days. After this period, the resulting peat and plant mixture is collected. The crop produced after the first vegetation period and the subsequently collected mixture are then combined together. The fodder thus produced may be applied as an additional component mixed in with traditional fodder or, in some circumstances, utilised alone.

Double cultivation of one peat layer results in a substantially more efficient use of the peat mass so that a considerably larger weight of fodder per unit peat mass is produced. Also, the resulting fodder has a much higher percentage of green vegetable matter so that the fodder is more nutritious. In general such fodder is better suitable for higher order breed animals in relation to fodder produced from peat utilising only a single vegetation period. In fact, the resulting fodder is suitable for single stomach animals such as pigs. As will be appreciated, single stomach animals are unable to digest a peat-plant mixture produced with only a single vegetation process.

Unexpectedly, it has been found that well processed peat-plant fodder after a single and preferably after a double vegetation period may be utilised as a supplement to food for humans. It may be added to such alimentary products as meal, groats, and rice. It is especially suitable for use in producing bread, dough, cakes, and other cooked, baked or fried products. Suitably, the peat-plant fodder will represent about 15% by weight of the total mixture.

Preferably, measures will be taken to eliminate bacteria and fungi. Any of the known methods of eliminating such substances may be utilised.

By use of fodder produced utilising a peat-plant mixture, a considerable reduction in use of conventional food stuffs may be achieved together with simultaneous improvement of the health giving properties of such food. Humans have been found to benefit considerably from the addition to peat-plant food stuffs to their diet in a similar manner to that observed in some animals, particularly single stomach animals such as pigs. The possibility also exists to regulate the calorific content of the food by varying the percentage of the added peat-plant material. Thus food can be produced containing only a small calorific content, e.g. food for slimming. Highly processed peat-plant food is more easily digested by humans when it is mixed with a further food component, such as groats and then subject to the usual heating processes such as boiling or baking.

A further improvement in the plant-peat food stuffs for addition to human food may be achieved in the final stages of its production. The plant-peat mixture may be crushed and water added containing lime, the resulting mixture being allowed to stand for 24 hours. The water is thereafter drained through a filter and flavourings may then be added in dependence upon the eventual use to which the food is to be put. The raw food material may be dried and packed.

The described methods are also capable of producing a peat-plant mixture having medicinal properties. Herbs and healing plants known in pharmacology may be utilised as the plants sown into the peat layer. Thin peat layers suitably of 40 to 75 mm thickness are then applied on the layer in which the herbs are sown. The layer is then allowed to vegetate for a period not exceeding 22 days. After this, the peat with the plants is collected and the mass comminuted. Following this, the mixture is disposed on an impermeable layer. Following the sowing of further herbs, a second vegetation process is allowed to take place. Then the peat layer is collected and comminuted again. After this, the peat mixture is disposed in a layer again and herb seeds sown in for a third time. After the vegetation period has been completed, collection and comminution is carried out as in the first two steps. Following this, the resulting mass is dried and packed.

Reinforcement of the medicinal properties of the peat-plant mixture can be obtained by allowing further vegetation processes to take place in the mixture in a similar manner to the first three vegetation processes described above.

The dried mass is suitable for use as a beneficial additive to food stuffs. The resulting dried mass may be applied in the raw state, or it may be utilised to form granules or pills.

An important feature of the described methods is the possibility of combining the medicinal properties of young plants together with their root systems with the properties of peat in a single production process. Since the process is simple, it may be easily carried out on the scale of mass production.

A further advantage of the methods results from the possiblity of using the peat-plant mixture in further processes for the cultivation of alimentary micro organisms such as algae, bacteria and yeast.

Production of yeast may be carried out by means of known techniques.

Another application for the peat-plant mixture is in the production of a biomass to produce sugar in order to produce alcohol by fermentation and distillation.

In the foregoing, reference has been made to laying a layer of peat on an impermeable surface. This impermeable surface may be mechanically hardened soil, a layer of foil such as synthetic plastics material, a layer of roofing paper, or a concrete surface.

Unless otherwise stated in the foregoing, the seeds may include those of oats, rye vetch, lupin, field peas, perco, soya, and similar plants. Preferably seeds of at least two types of plant will be sown together. It is possible to mix the seeds with the peat before the formation of the peat layer, for example by using conventional mixing and sowing machines equipped with seed metering devices, or it is possible to sow the seeds when the wheat layer has been formed.

Furthermore, the seeds may be sown either in a dry ungerminated condition or at the stage of initial germination. Germination may be initiated in special containers or elsewhere. When sowing seeds which have already germinated, special care is needed to avoid damage to the seeds. The advantage of adopting this technique is the reduction of the necessary vegetation period in the peat field and a consequent increase in production speed of edible matter.

As in the methods described in United Kingdom patent specification No. 80.02710, during vegetation period natural germination of the seeds takes place in the layer as well as the natural development of the root systems of the plants. In parallel with the germination of the seeds, a biological process initiated by the development and presence of the plant root systems proceeds in the layer of peat. This process has not been fully investigated but has the effect of transforming the peat layer into a substance suitable for digestion.

I claim:

1. A method of producing a foodstuff for human or animal consumption, comprising the steps of:
   forming a layer of peat having a thickness in the range of about 40 to about 200 millimeters on a surface substantially impermeable to plant roots;
   sowing into the peat layer seeds of at least one quick germinating plant of a type such as to produce strong root systems at a rate of at least about 900 kilograms of seeds per hectare; and
   vegetating the seeds for a period in the range of from 10 to 21 days;
   whereby the layer of peat with germinated seeds in usable as a foostuff.

2. A method according to claim 1 wherein the seeds are sown in the peat after they have started to germinate.

3. A method according to claim 1 wherein the seeds are sown in a dry condition.

4. A method according to claim 1 wherein the peat layer has a thickness of from 40 to 75 mm.

5. A method according to claim 1 in which said layer is sterilised before sowing of said seeds.

6. A method according to claim 5 in which after the vegetation period the resulting peat-plant mixture is added to food for human consumption.

7. A method according to claim 6 in which said mixture is added to at least one of, rice, other grains and groats.

8. A method according to claim 6 in which: said mixture is disaggregated and placed in lime water for at least 24 hours; the mixture is separated from the liquid; and the mixture is dried for addition to other foodstuff.

9. A method according to claim 8 wherein flavouring is added before drying of said mixture.

10. A method according to claim 8 wherein the dried mixture represents 15% by weight of the total when mixed with other foodstuff.

11. A method according to claim 1 in which: after said vegetation period those parts of the plants protruding above said layer are cropped, broken up and dried; further seeds are sown in said layer and allowed to remain for a vegetation period of from 10 to 21 days; the peat layer and germinated seeds is collected; and the plant parts collected after the first vegetation period are added to the peat and plant mixture.

12. A method according to claim 1 in which said seeds are those of plants having medicinal properties and/or herbs.

13. A method according to claim 12 wherein after said vegetation period the layer is collected and disaggregated and then an additional cultivation process is carried out as follows: the peat-plant mixture is spread again in a layer, whereafter further plant seeds are sown and cultivated and the resulting peat-plant layer is collected and disaggregated.

14. A method according to claim 13 in which a second said additional cultivation process is performed.

15. A method according to claim 14 in which at least one yet further said additional cultivation process is performed.

16. A method according to claim 13 in which following the final cultivation process the peat-plant mixture is dried.

17. A method according to claim 13 in which the disaggregation steps are achieved by grinding.

18. Foodstuff produced by the method of claim 2.

* * * * *